United States Patent [19]

Schiel et al.

[11] E Patent Number: Re. 33,034

[45] Reissued Date of Patent: Aug. 29, 1989

[54] PRESS ROLL FOR WEB MATERIAL WITH CLAMPED PRESS JACKET

[75] Inventors: Christian Schiel; Hans Flämig; Udo Grossmann; Joseph Müllner, all of Heidenheim; Karl Steiner, Herbrechtingen, all of Fed. Rep. of Germany

[73] Assignee: J. M. Voith GmbH, Fed. Rep. of Germany

[21] Appl. No.: 239,135

[22] Filed: Aug. 31, 1988

Related U.S. Patent Documents

Reissue of:

[64] Patent No.: 4,625,376
Issued: Dec. 2, 1986
Appl. No.: 717,761
Filed: Mar. 28, 1985

[30] Foreign Application Priority Data

Jan. 19, 1985 [DE] Fed. Rep. of Germany ..... 3501635

[51] Int. Cl.[4] ..... A61F 13/20; D04H 1/22

[52] U.S. Cl. ..... 241/119; 26/104; 241/118; 241/131

[58] Field of Search ..... 29/119, 118, 130, 131; 26/104; 100/176, 155 R; 51/364; 101/415.1

[56] References Cited

U.S. PATENT DOCUMENTS 3,452,414 7/1969 Schiel ..... 29/119
4,518,460 5/1985 Hauser et al. .
4,555,305 11/1985 Steiner et al. .

FOREIGN PATENT DOCUMENTS 1561674 4/1970 Fed. Rep. of Germany .
1923784 12/1970 Fed. Rep. of Germany .
3102526 8/1982 Fed. Rep. of Germany .
147 of 1897 United Kingdom ..... 29/118

*Primary Examiner*—Timothy V. Eley
*Attorney, Agent, or Firm*—Ostrolenk, Faber, Gerb & Soffen

[57] ABSTRACT

A press roll for acting in opposition to a counter roll. The press roll has a support member which is supported at its opposite ends. The support member is stationary in certain most embodiments and rotatable in one embodiment. A flexible, liquid-tight endless press jacket is wrapped around the support member. At each lateral end of the press roll, the press jacket is fastened to the outward end of a supporting disk, which is rotatably mounted on the support member. The lateral edge zones of the press jacket are both deformed radially inwardly around the outside of the respective supporting disks and each edge zone is clamped there by a annular clamping flange. To facilitate deformation of the edge zones, at least one of the edge zones terminates in a series of tongues separated by cutouts arrayed around the roll. Coiled tension springs engage the edge zone and/or the tongues to pull them in the direction toward the axis of the roll.

30 Claims, 3 Drawing Sheets

PRESS ROLL FOR WEB MATERIAL WITH CLAMPED PRESS JACKET

Matter enclosed in heavy brackets [ ] appears in the original patent but forms no part of this reissue specification; matter printed in italics indicates the additions made by reissue.

BACKGROUND OF THE INVENTION

The present invention relates to a press roll for treating web material, and preferably for removing water from a web of fibers. The press roll forms a press nip with a counter roll. The press roll has an elongate support member which is either stationary or rotatable. The press roll has an endless flexible, liquid-impervious press jacket which is disposed on the fixed or rotatably mounted support member extending through the jacket. The invention concerns the clamping of the lateral ends of the press jacket and to the design of those ends.

According to Federal Republic of Germany DE-OS No. 19 23 784, if a stationary rather than a rotary support member is present, the flexible press jacket slides over the support member in the region of the press nip when the support member presses the press jacket against the counter roll. For this purpose, as taught in Federal Republic of Germany DE-OS No. 31 02 526, a press shoe which is movable in the radial direction is provided on the support member, with the press jacket sliding over that shoe. The slide surface of the press shoe is usually concave in shape, corresponding to the curvature of the counter roll. As a result, the press nip has a certain length in the direction of travel of the web, i.e. an extended press nip is formed. The cross sectional shape of the support member may be any desired shape, for instance rectangular, tubular or I-shaped.

If the support member is rotatably mounted rather than fixed, and if it has the shape of a circular-cylindrical rolling body, then when the support member presses the press jacket against the counter roll, the support member rolls in the region of the press nip against the inner side of the press jacket (as shown in Federal Republic of Germany DE-OS No. 15 61 674). In the construction in the German application the press jacket is perforated. The press roll of the invention, in contrast, always has a liquid-impervious press jacket, since its inner side must, as a rule, carry a film of lubricant, and none of the lubricant must penetrate outward from the inside of the press roll. Otherwise, there would be the danger of contamination of the web which is to be treated.

Known press rolls have on each end of the support member a press jacket support element which is in the form of a disk which is mounted for rotation. According to Federal Republic of Germany DE-OS No. 19 23 784, each of the two ends of the press jacket has a radially inwardly deformed, spatially curved, edge zone which has a bead, in the manner of an automobile tire. This edge zone is attached by means of a clamping flange to one end of the jacket support element. The attachment is liquid-tight, i.e. the press jacket lies against the jacket support element in the region of an end annular sealing surface, the edge zone having the bead extends relatively far toward the axis of the roll, i.e. the inner circumference of the flexible press jacket is substantially smaller in the region of the end opening than in the region of the press zone. This makes it difficult to pull the press jacket over the support member and over the elements provided on the support member for the guidance of the press jacket, for instance, guide rolls in the case of the known press roll.

In the press roll of the invention, the press jacket, as known from Federal Republic of Germany DE-OS No. 31 02 526, is preferably made of a reinforced, relatively hard plastic, for instance polyurethane, and it preferably has a relatively stiff fabric reinforcement. Press jackets of this construction are preferred, particularly in roll presses having extended press nips, since they withstand the high frictional stresses in continuous operation relatively well. However, the liquid-tight connection of such a press jacket support element, preferably jacket support disks, affords difficulties. It has been attempted, corresponding to the construction in Federal Republic of Germany DE-OS No. 15 61 674, to fasten the two ends of the flexible press jacket, not to an outer end side, but to an outer cylindrical circumferential side of the jacket support disks. The advantage of this method is that deforming the ends of the press jacket in the direction toward the axis of the roll is not necessary. A disadvantage, however, is that the required liquid tightness can be obtained only at great expense. It is very difficult to manufacture the inner circumference of a press jacket in such a way that it exactly fits the outside diameter of the jacket support disks. This is quite expensive because the press jacket must be periodically replaced by a new one because of wear.

SUMMARY OF THE INVENTION

The object of the invention is, therefore, further to develop the above-described type of press roll such that upon assembling the press roll, the press jacket can be easily pulled over the support member with the least possible expenditure of force, and that nevertheless a liquid-tight connection can be produced by simple means between the lateral ends of the press jacket and the jacket support elements.

The invention concerns a press roll for forming a press nip against a counter roll. The press roll includes a main support member which extends along the press roll between the opposite ends of the press roll, and there are means that support the support member to either rotate or be stationary, as a particular embodiment may require. There is an endless, flexible, liquid-tight press jacket wrapped around the support member. It has lateral ends that extend beyond the ends of the support member. The jacket is rotatable, either with respect to the support member in some of the embodiments or along with the support member in another embodiment. But in all events it rotates over the support member. At each end of the support member, there is a respective rotatable press jacket support element in the form of a disk. The support elements for the jacket are laterally outside the press nip. Each support element has a periphery over which the press jacket passes and has an outwardly facing end, facing away from the support member, to which the press jacket is clamped after the press jacket is installed on the support member. The press jacket rotates with the disks to which it is clamped.

At each of its lateral edges, the press jacket has an edge zone which extends past the periphery of the jacket support element and then extends radially inwardly past the outside of the jacket support element, and the press jacket there defines an annular end sealing surface.

There are clamping means that are located outward of the outside of the jacket support element and which are clampable against the annular end sealing surface of the press jacket for clamping that surface against the outside of the jacket support element and thereby defining a liquid-tight enclosure inside the press jacket.

At at least one and possibly at both of the lateral ends of the jacket, the jacket edge zone is urged radially inwardly toward the axis of the press roll for forming the end sealing surface of the edge zone. Such inward urging positions the edge zone for subsequent clamping by the clamping means.

The edge zones of the press jacket are urged radially inwardly by a plurality of biasing means distributed circumferentially around the roll and those biasing means preferably comprise tensioning elements in the form of tension springs.

The edge zone may be shaped to form a plurality of tongues around the circumference of the roll by defining or forming cutouts between the adjacent tongues, and the basing means are engaged to the tongues for moving them inwardly. To attach the press jacket to the supporting disks, the tongues are inserted between the disk and a clamping flange which is initially spaced from the outside of the jacket supporting disk. This initially creates a rounded transition of the press jacket between its laterally extending portion and its inwardly folded tongues, rather than a sharp fold. The radially inwardly directed portion of the edge zone is then clamped by the clamping flange.

All of these solutions employ the concept that the end sealing surface on the press jacket at its lateral end is to be shaped only after the press jacket has been pulled over the support member and over the jacket support elements, which are preferably jacket support disks. This is done at least for the one end of the press jacket which is toward the front end, that is the end that is last to be covered and toward which the jacket is pulled during the pulling over of the support member. The other end of the press jacket could, if necessary, have been deformed prior to the pulling over step, in order to form that end sealing surface. Preferably, however, both ends of the press jacket are treated in the same way, i.e. the rear end of the jacket is also deformed only after the pulling over. In that case, the press jacket is pulled as a tubular, merely singly curved structure onto the support member and only thereafter are the spatially curved edge zones shaped. Such a procedure is already known in connection with other types of rolls from U.S. Pat. No. 3,452,414. In that case, however, as in Federal Republic of Germany DE-OS No. 15 61 674, the press jacket is porous. It consists exclusively of a screen netting. Thus, there is no need in this prior art for sealing off the inner space surrounded by the press jacket. Accordingly, no measures are taken there for forming a smooth sealing surface, so that the end edge zone of the netting jacket forms itself in folds.

The following must also be taken into account. The formation of a spatially curved edge zone is relatively simple with a pure screen netting since such a netting is known to be easily shaped. On the other hand, the shaping of a liquid-tight press jacket which consists of a relatively hard, reinforced plastic is substantially more difficult. Here, much more than for a netting jacket, there is the danger that wrinkles will form upon the bending of the edge zone of the press jacket in the direction toward the axis of the roll. Therefore, the method and construction of the invention were originally considered unusable in practice. However, after lengthy experiments, it was found that there are, nevertheless, various solutions for producing a wrinkle-free, smooth end sealing surface after the pulling of the press jacket onto the support member, with the formation of a spatially curved transition zone toward the normal cylindrical part of the press jacket.

The first solution of the invention is that at at least one of the two lateral edge zones of the press jacket, a plurality of fastening points are provided, for instance holes, eyes, clamping places, or the like for the application of tensioning or pulling elements, which are preferably coil tension springs. These tensioning elements are so tensioned in the radial direction after being pulled over that they exert tensile forces in a direction toward the axis of the roll on the edge zone of the press jacket. In this way, the edge zone of the press jacket is deformed radially inwardly around the outer edge of the jacket support element. In this case, it is important that a much larger number of tensioning elements, than in the construction known from U.S. Pat. No. 3,452,414, namely, at least 30, be arranged at uniform distances apart on each end of the roll. The stiffer is the material of the press jacket, the greater should be the number of tensioning elements. From 45 to 72 tensioning elements are preferably provided, i.e., each edge zone of the press jacket is to be subdivided by the tensioning elements into preferably 45 to 72 sections, regardless of the diameter and thus of the circumference of the roll. The smaller is the diameter of the roll, the smaller the distance between each two adjacet tensioning elements should also be, because the smaller is the diameter of the roll, the more difficult it is to shape a wrinkle-free, spatially curved edge zone on the press jacket.

With an extremely large number of tensioning elements, it is possible to upset the outermost edge of the press jacket in the peripheral direction with deformation of the jacket toward the axis of the roll. It is therefore possible to compress the end zone of the jacket in the circumferential direction and to thereby shrink it to a smaller diameter, without forming wrinkles. Thus, a smooth and sufficiently wide end sealing surface is obtained which forms one of a pair of sealing surfaces together with the outward end of the jacket support element.

After the edge zone of the press jacket has been pulled sufficiently far in the direction toward the axis of the roll in the manner described, the press jacket is fastened in this position by means of the clamping flange.

In a second solution, and preferably before the pulling of the press jacket over the support member, numerous laterally extending tongues are formed on one or both of the lateral edge zones of the press jacket by cutting out a plurality of approximately triangular or trapezoidal, or else rectangular, cutout from the edges of the jacket uniformly round the circumference. For mounting of the press jacket, the clamping flange is premounted on and spaced from the end of the corresponding jacket support element so that an annular, substantially radial gap of approximately the thickness of the press jacket is produced. After the press jacket is pulled over the support member, the tongues are first bent over in the direction toward the axis of the roll and are then pushed into said slot. Since the material of the press jacket is relatively stiff but nevertheless flexible, the tongues are not kinked thereby. Instead, a rounded transition region or bead-like bulge is formed between the cylindrical part of the press jacket and the inwardly bent tongues. In this way, it is now possible through the action of pressure forces on the transition region to push the tongues so far into the slot that the deepest regions of the cutouts between the tongues extend at least a small distance into the annular slot. In this way, again, the edge zone of the press jacket is upset, and more precisely, the region of the edge zone which is free of cutouts is upset, i.e. the end pair of sealing surfaces is formed between the edge of the press jacket and the jacket support element, so that the press jacket can now be fastened by the complete mounting of the clamping flange.

Essential to this second solution is the presence of a sufficiently large number of tongues. The stiffer the material of the press jacket, the more tongues should be provided. The length of the tongues, i.e. the depth of the cutouts, may be any depth desired, with a preferred order of magnitude of 50 to 100 mm. The total length of the press jacket, measured transverse to the circumferential direction, i.e. longitudinally of the press roll, must be selected one tongue length or two tongue lengths larger. The width ratio between the tongues and the cutouts may also be any ratio desired. In experiments, a width ratio of about 1:1 has proven satisfactory. Although it is useful also to round the bottoms of the cutouts, angular cutouts are also possible.

A third solution, which has proven best in experiments, corresponds approximately to a combination of the first and second methods, in that both tensioning elements and tongues are provided, in an equal number at each lateral end of the roll. Each tensioning element is fastened to the tip of a tongue or is simply suspended there. The mounting of a press jacket on the support member is done practically in exactly the same way as in the first solution described above. As compared with that first solution, however, important additional advantages are obtained by means of the tongues:

1. The tensile force applied by the tensioning elements is distributed via the tongues over a larger circumferential region of the edge of the press jacket. As a result, the above-described deformation of the edge zone of the press jacket for forming the end sealing surface can be effected, free of wrinkles, with great reliability. The cutouts between the tongues, which substantially facilitate the deforming, also contribute to this. For this reason, if the press jacket consists of relatively thick and, in particular, stiff material, the tongues can, as a general rule, not be dispensed with.

2. The tongues can extend so far in the direction toward the axis of rotation of the roll that the places of attachment for the outer ends of the tensioning elements lie a radial distance inside of the clamping flange and therefore they are no longer covered by the flange. In this way, the tensioning elements can be removed without difficutly after the clamping flange is screwed to the jacket support disk, because after completion of the assembly of the press roll of the invention, the tensioning elements are no longer required. By the removal of the tensioning elements, one possible danger of accidents is eliminated. On the other hand, in the first solution described above, there is the possibility of covering the entire length of the tensioning elements by the clamping flange.

The explanations given in the following sections A to D apply to all three above-described solutions.

A. The pair of sealing surfaces can be developed conically to facilitate the deformation process. However, deformation of the edge zone of the press jacket is generally possible even if the pair of sealing surfaces lies in a plane normal to the axis.

B. The obtainable width of the sealing surface at the edge of the press jacket is dependent upon the diameter, and thus upon the circumference, of the roll. The greater is the diameter of the roll and, consequently, the smaller is the curvature of the press jacket in the circumferential direction, the wider will be the sealing surface which can be produced without the danger of the formation of wrinkles. The customary roll diameters are between about 0.5 and 2 m and the sealing surfce widths which can be produced are approximately between 5 and 40 mm. The sealing surfaces of this width, even if a width of only about 5 to 10 mm is reached, are sufficient to obtain a complete seal between the flexible press jacket and the jacket support elements. This is obtained with the invention because the edge zone of the press jacket is so uniformly deformed, despite the high stiffness of the material of the jacket, that it rests sufficiently snugly agaisnt the end of the jacket support element.

C. As already mentioned, the press roll of the invention can be developed either with a stationary support member, for a roll press preferably having an extended press nip, or with rotatable support member. In the latter case, the support member and the press jacket can rotate with different speeds of rotation. This last-mentioned construction can substitute for the previous rolls which have firmly applied coverings (for instance, of rubber, plastic, or the like). Those previous rolls have the disadvantage that, after a certain amount of wear of the covering, they must be removed from the machine in order to repair or replace the covering. Therefore, a spare roll must be available for each roll of this type. This is not longer necessary due to the invention, since it is now possible to replace the press jacket, which is in the form of a loose covering, by a new one within a short period of time without it even being necessary to remove the press roll from the machine.

D. As already mentioned, it was originally attempted to fasten the edge zones of the liquid-tight press jacket, like that shown in Federal Republic of Germany DE-OS No. 15 61 674, to the outer cylindrical circumferential surface of the jacket support element. However, for a press with an extended nip press zone, high tensile stresses occur in the press jacket upon its rotation through the press zone, particularly in the regions between the press zone and the jacket support elements. These continuously varying tensile stresses cause premature wear of the press jacket, both at the edges of the press zone and at the clamping places between the jacket support elements and the clamping flanges. With the invention, it is now surprisingly possible to substantially avoid those tensile stresses and the resulting wear. This is probably due to the fact that, upon the described deformation of the edge zones of the press jacket, a spatially curved transition is formed, from the normal cylindrical region of the press jacket to the end sealing surface, as already mentioned, and that the press jacket generally bulges somewhat in bead shape in the transition zone. In this way, the press jacket is imparted a substantially improved axial yieldability.

If tongues are formed on the press jacket as described above, then further features can be applied. The bottom of each cutout or of a part of the cutout can be used for centering the press jacket. For this purpose, on the one hand, the size and position of the cutouts in the press jacket and, on the other hand, the arrangement of the projections on the end of the jacket support element are adapted to each other. In this way, good concentricity of the press jacket is obtained in a particularly simple manner and without any particular expnediture of time. In this connection, the press jacket, particularly in the designs with a stationary support member, is already worn after an operating period in the order of magnitude of a few weeks or months, and the jacket must be replaced. This replacement can be effected by simple means and in a short time in accordance with the invention, without it being necessary to remove the roll from the machine.

In a variant of the first solution described above, the press jacket can also be centered without its having tongues. For this purpose, a rotating centering surface must be developed on the jacket support disk, and the edge of the press jacket resting against that surface. This construction, however, requires greater care and more time upon clamping of the press jacket.

Other objects and features of the invention will be explained below with reference to the embodiments shown in the accompanying drawings.

DESCRIPTION OF THE PREFERRED EMBODIMENTS

Figure 1:
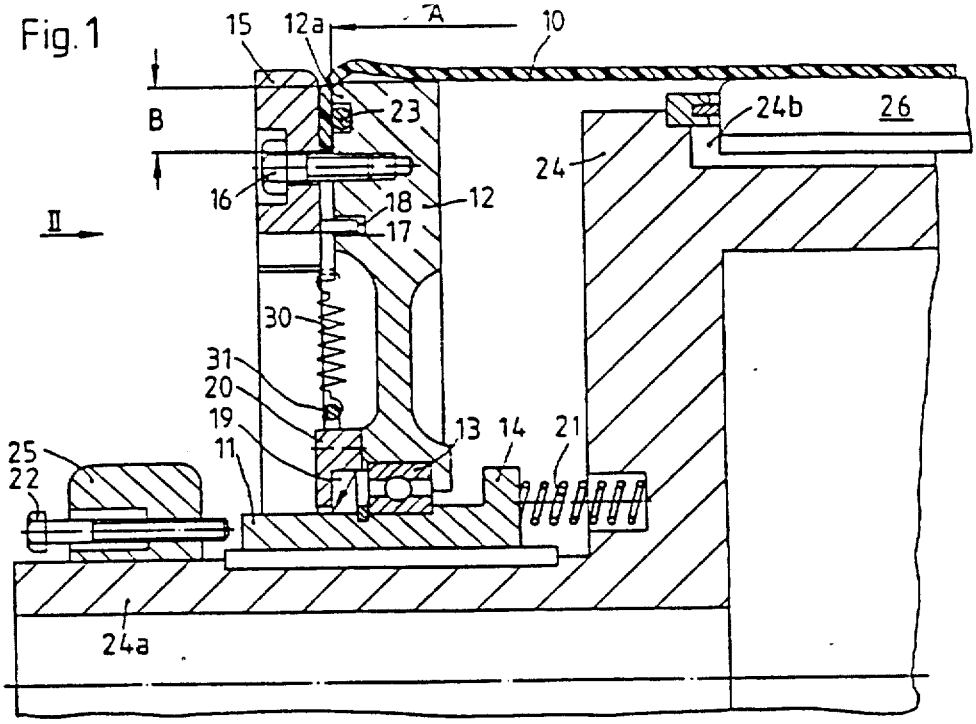
FIG. 1 is a partial radial section through an end of a press roll having a jacket support disk and tensioning elements.
Figure 2:
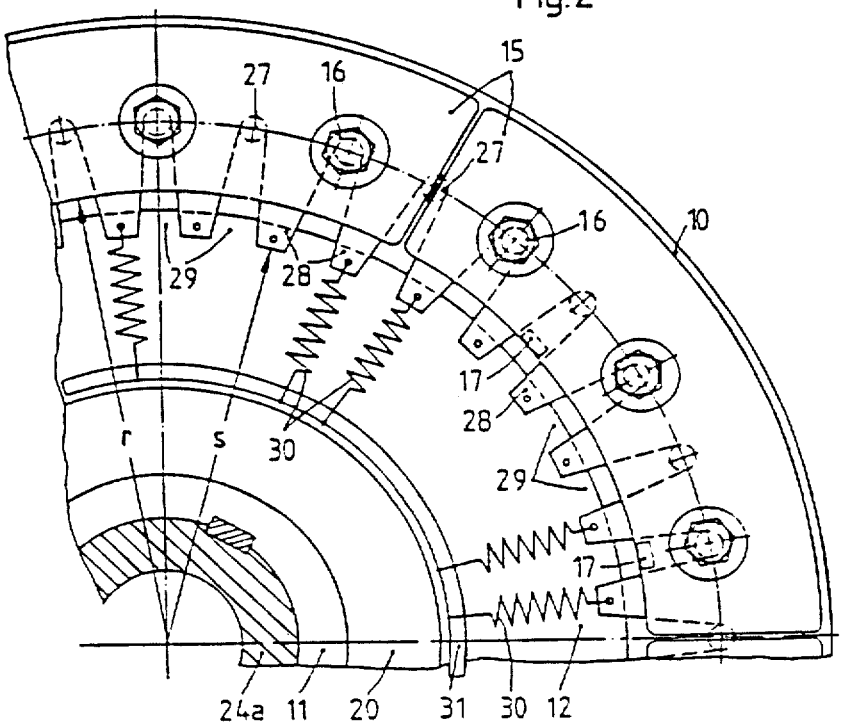
FIG. 2 shows a section of the jacket support disk, seen in the direction of the arrow II of FIG. 1.

The press roll shown in FIGS. 1 and 2 has a nonrotating support member 24, only one end of which is visible. The support member 24 is supported at its opposite two ends by a respective journal pin 24a which is received in a bearing pedestal 25. On its periphery or outside, the support member is provided in known manner with a recess 24b within which a press shoe 26 is arranged. The length of that shoe along the press roll corresponds approximately to the width of the web of paper to be treated. Around the support member 24 and the press shoe 26, there travels an endless tubular press jacket 10. Due to the action of a pressure fluid upon the press shoe 26, it presses the press jacket 10 against a counter roll (not shown).

At each longitudinal end of the press roll, there is a bearing ring 11 on the journal pin 24a which is arranged for translation but not for rotation. A jacket support element or disk 12 is rotatably mounted on the bearing ring 11 by an anti-friction bearing 13. At the outward end or side of the jacket support disk 12, the radially inwardly deformed edge zone of the press jacket 10 is fastened by means of a clamping flange 15 which clamps on the jacket 10. The flange 15 is held by screws 16 which extend through the flange and are received in openings in the disk 12. To facilitate its mounting, the clamping flange 15 can be divided into accurate segments of convenient size. Furthermore, the segments can have axially extending projections 17, which fit into an annular groove 18 on the end of the jacket support disk 12.

The inside of the press roll, which is defined by the press jacket 10 and the jacket support disks 12, is to be sealed from the outside. The press jacket 10 comprises a liquid-impervious, flexible sheet plastic, for instance of polyurethane. It is preferably reinforced with a dimensionally stable support fabric which is composed in known manner of circumferential and longitudinal threads. The outer or outward end of the jacket support disk 12 and the edge zone of the press jacket 10 together form a pair of sealing surfaces having a radial width B in FIG. 1. To assure tightness with even greater certainty, an annular groove is provided in the outer end of the jacket support disk and an O-sealing ring 23 is arranged in the groove. The O-ring presses out against the press jacket 10 and the flange 15. Finally, outside of the anti-friction bearing 13, there is a shaft sealing ring 19, which rests on a housing ring 20 that is fastened on the jacket support disk.

For axial tensionign of the press jacket 10, coil compression springs 21 are clamped between the support member 24 and a flange 14 of the bearing ring 11. To facilitate mounting of the press jacket 10, at least one pressing screw 22 is provided in the bearing pedestal 25. The screw can bring the bearing ring 11 together with the jacket support disk 12, temporarily somewhat closer to the support member 24.

Figure 3:
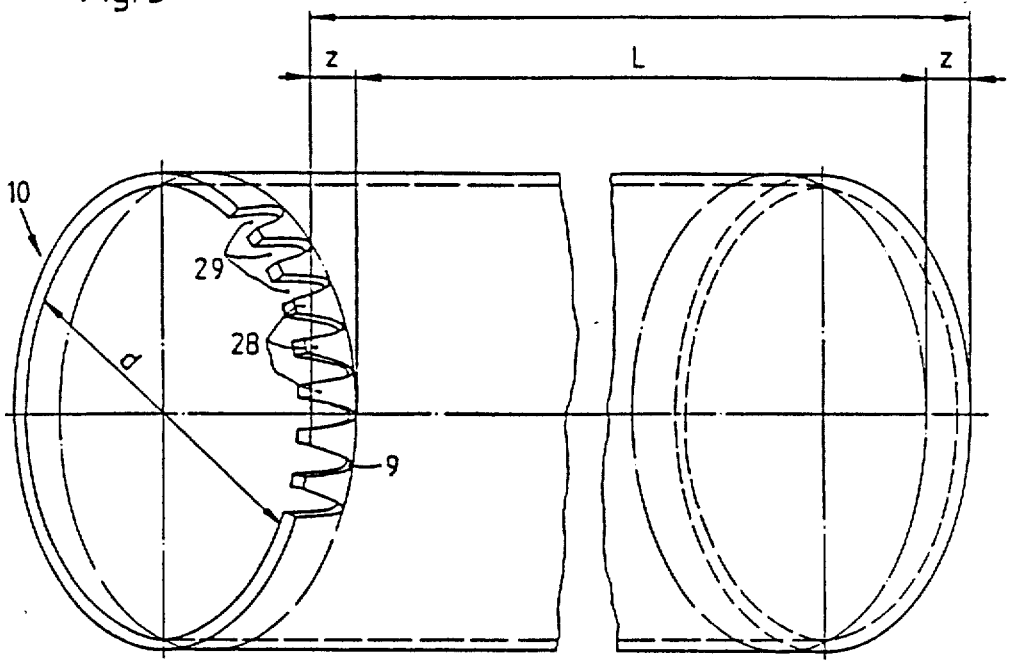
FIG. 3 shows the press jacket by itself, in an oblique view.

FIG. 3 shows the press jacket 10 before it has been pulled onto the support member 24. In this state, it has an elongate, approximately cylindrical base shape. At its two ends, numerous, approximately triangularly shaped cutouts 29 are formed, so that approximately trapezoidal tongues 28 remain, and the tongues extend in the paraxial direction. For simplifying the drawing, the press jacket has been shown as a circular cylinder in FIG. 3 (in oblique view). However, due to the flexibility of the material, its actual cross section will differ to a greater or lesser extent from a circular shape. As known from Federal Republic of Germany DE-OS No. 33 11 998 (corresponding to U.S. Ser. No. 592,629, filed Mar. 23, 1984), the total circumferential length of the inside of the press jacket, which is a function of the inside diameter d shown in FIG. 3, is selected so that there is a certain distance between the press jacket and the support member 24. Furthermore, the outside diameter of the jacket support disks 12 is usually slightly smaller than the inside diameter d of the press jacket 10. In this way, the press jacket 10 can be pulled over the support member 24 and the jacket support disks 12 using slight force.

The length L of the part of the press jacket which is free of cutouts 29 is related to the approximate distance A (FIG. 1) between the outer end surfaces of the jacket support disks 12 and to the radial width B of the sealing surface. Due to the aforementioned displaceability of the bearing rings 11, the distance A can be varied. The length z of the tongues 28, and thus the total length G of the press jacket 10, is selected so that in the completely mounted condition of the press jacket, the tongues 28 extend radially inward beyond the inward edge of the clamping flange 15. Thus, the distance s from the axis of the press roll to the ends of the tongues 28 is less than the distance r from the axis of the press roll to the radially inner periphery of the annular clamping flange 15 (FIG. 2).

One possible way to manufacture the cylindrical base shape of the press jacket is now described. A tube with a length that is a multiple of the total length G is produced. The required piece of length G, or approximately the length L (if, in accordance with FIG. 5, the tongues 28 are not required), is then cut off.

The press jacket 10 of the elongate shape shown in FIG. 3 is changed into the shape shown in FIGS. 1 and 2, wherein the lateral edge zones of the press jacket part extend radially inward in the manner of a flange and form a smooth sealing surface. This is accomplished by the following steps:

The clamping flange segments 15 are either completely removed from or are brought a great distance from the jacket support disks 12. One tongue 28 after the other, or in each case, two paired tongues which are radially opposite, is (or are) bent radially inward around the rounded radially and axially outer edge 12a of the jacket support disk 12. A coil tension spring 30 is fastened to the tip of each tongue 28. After stretching and tensioning of the spring, its other end is attached to a wire ring 31 which loosely surrounds the bearing ring 11 or (as shown in FIGS. 1 and 2) the housing ring 20. Some of the springs 30 have been omitted in FIG. 2 in order to simplify the drawing.

Figure 5:
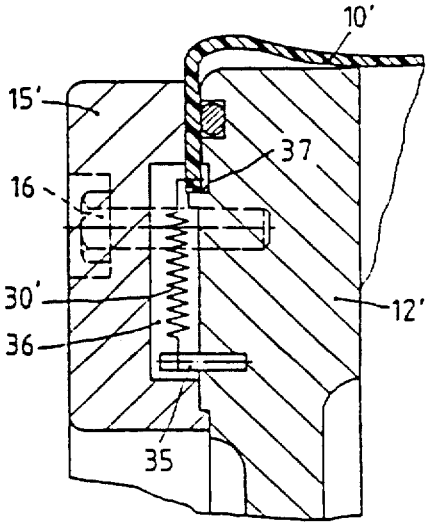
FIG. 5 shows a second variant of the press roll with press jacket of FIG. 1 with tensioning elements but without tongues on the press jacket.

In a different embodiment, the radially inner ends of the coil tension springs could also be fastened to the housing ring 20, similar to the manner shown at 35 in FIG. 5. The plurality of tensile forces acting radially inward on the edge zone of the press jacket generates the spatially curved inward shape of the edge zone, in accordance with FIG. 1. The material is upset in the region of the radial width B of the sealing surface, while it usually bulges somewhat in bead-like manner radially outside of the sealing surface.

As seen from FIG. 2, a projection 27 which is in the form of a bolt, is arranged in the axially outer end of the jacket support disk 12 between every pair of screws 16. The number of screws 16 and bolts 27 together equals the number of tongues 28 or cutouts 29. The arrangement of the screws 16 and the bolts 27 are arranged so that they fit exactly alternately into adjacent cutouts 29. The screws 16 and the bolts 27 are preferably arranged on the same pitch circle so that the depth z (FIG. 3) of all cutouts 29 can be the same. However, one can also deviate from this. It is also advantageous, as shown in FIG. 2, to provide an equal number of screws 16 and bolts 27 and to distribute them alternately on the circumference. It is further advisable to make the diameters of the screws 16 and the bolts 27 identical. In this way, all cutouts 29 of the press jacket 10 can have the same shape.

Upon the previously described shaping of the edge zone of the press jacket 10, the tongues 28 are pulled so far in the direction toward the axis of the roll that the bottoms 9 (FIG. 3) of the cutouts 29 rests against the bolts 27, and against the screws 16 if the screws are not removed. This very rapidly provides a central seating of the press jacket 10 and thus good concentricity in operation. After the clamping of the edge zone of the press jacket 10 between the jacket support disk 12 and the clamping flange 15, the temporary springs 30 and the loose wire ring 31 can be removed. Finally, the push screw 22 is loosened from the bearing ring 11 so that the compression springs 21 can bias the press jacket 10 outwardly in the lateral direction. If the clamping flange 15 is not removed from the jacket support disk 12 for the mounting of the press jacket 10, so that the loosened screws 16 remain on the disk 12, then the screws 16 should by themselves be sufficient for the centering of the press jacket 10, and one could dispense with the separate projections 27.

Figure 4:
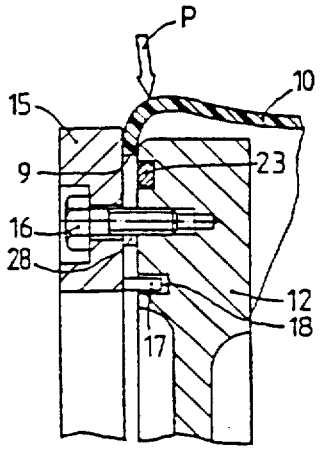
FIG. 4 shows a first variant of the press roll with press jacket of FIG. 1, without tensioning elements.

FIG. 4 shows that the press jacket 10 can also be deformed without tension springs 30. In this case, the original shape of the press jacket is as shown in FIG. 3. For the mounting of the press jacket, the clamping flange 15 remains on the jacket support disk 12. The slot between the flange 15 and the disk 12 is adjusted by means of the screws 16 so that the tongues can be pushed into the slot. For this procedure, it is advisable to first push the bearing ring 11 together with the jacket support disk 12 a distance toward the bearing pedestal 25 (FIG. 1). After the tongues have been pushed into the slot, the bearing ring 11, together with the jacket support disk 12, is pushed by the push screws 22 back in the direction towaqd the support member 24 (to the right in FIG. 4). As a result, the press jacket 10 bulges out at the periphery of the jacket support disk 12. Using a suitable tool, which is indicated symbolically in FIG. 4 by the arrow P, it is now possible to push the tongues 28 and the edge region of the press jacket forming the end sealing surface further into the slot until the bases 9 of the cutouts 29 rest against the bolts 27 (FIG. 2) and the screws 16. Then the clamping ring 15 is again clamped fast while the push screws 22 are loosened. For this method, the length z of the tongues 28 can be selected to be somewhat smaller than in the embodiment of FIGS. 1 and 2, since the tongues need not extend radially inward beyond the clamping flange 15.

In FIG. 5, the shaping of the edge zone of the press jacket 10′ is again effected by tension springs 30′. In this case, however, the press jacket 10′ does not have any tongues, i.e. its original length is only slightly greater than the measurement L of FIG. 3. The coil tension springs 30′ have one of their ends placed directly in the lateral edge of the press jacket. After the springs are tensioned, the other end of each spring is attached to a respective bolt 35. The bolts are inserted in the jacket support disk 12′. In the region of the springs 30′, the clamping flange 15′ is provided with a radially and axially wide annular groove 36 large enough that it can cover the springs 30′ without contacting them. After the end of the mounting process, they remain in the position shown. For centering the press jacket 10′, a circumferential centering surface 37 is formed on the jacket support disk 12′.

Figure 6:
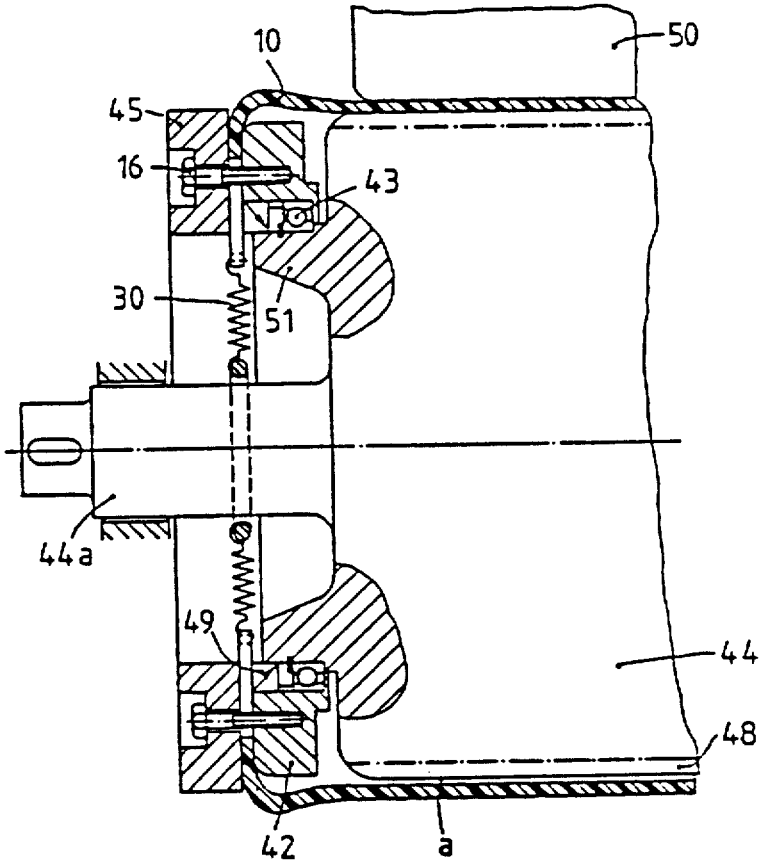
FIG. 6 shows a third variant of the press roll, with a rotating support member.

FIG. 6 shows the application of the invention to a press roll which is turnable as a whole and which has a loose covering in the form of the above-described press jacket 10. This embodiment differs from the others because the support member is developed as a rotatably mounted and therefore circular-cylindrical roll body 44 whose journal pin 44a can, if necessary, be coupled with a drive (not shown). The basic shape of the press jacket 10 is the same as shown in FIG. 3. The end liquid-tight closure of the inner space defined by the press jacket 10 could, in principle, be developed in exactly the same way as in FIGS. 1 and 2 or 4 or 5, using a bearing ring 11 that is displaceable on the pin 44a and a jacket support disk 12 mounted thereon. However, differing from this, in FIG. 6, a bearing ring 51 is developed on the roll member 44. Over the ring 51 there is mounted, through anti-friction bearing 43 and adjacent sealing ring 49, an annular jacket support element 42 mounted concentric to the roll member 44. The press jacket 10 is fastened by clamping ring 45 and screws 16 to the outer end surface of the jacket support element 44. This attachment and the preceding shaping of the press jacket 10, for instance by use of the tension springs 30, is effected in the same way as has been described above with reference to FIGS. 1 to 5. Mounting of the jacket support element 42 at a greater distance from the axis of the roll than in FIG. 1 is possible since only a small difference in speed of rotation occurs between the press jacket and the roll body 44.

At the top of FIG. 6 can be noted a small piece of a counter roll 50, which forms a press nip with the press roll. In the circumferential region outside the press nip, there is a small distance a between the press jacket 10 and the roll body 44 since the inside diameter d (FIG. 3) of the press jacket 10 is greater than the outside diameter of the roll body 44. Axial tensioning of the press jacket 10 is dispensed with in FIG. 6. If necessary, however, axial displaceability of the bearing ring 51 relative to the roll body 44 could be provided.

The roll body 44 can be made completely of metal and can therefore be made without the fixed covering, for instance of rubber, plastic, or the like, which has frequently been necessary. The function of that covering is now assumed by the press jacket 10 which rotates loosely with the roll body. However, in order to obtain special effects, e.g. upon the travel of the web to be treated through the press nip, it is also possible to provide the roll body 44 with an additional fixed covering 48, as indicated as an alternative by dot-dash lines in FIG. 6. There are also many possibilities of variation by the selection of given pairs of material for the press jacket 10 and for the fixed covering 48.

In all the Figures, the lines which are generally required for feeding and removal of lubricating and/or cooling liquid, for instance, for cooling the roll body 44, have been omitted. Lubrication of the inside of the press jacket 10, particularly upon its passage through the press nip, is indispensable in the case of a stationary support member 24, 26 (FIG. 1). It may also be advisable for a rotating support member (FIG. 6). If such lubrication of the press jacket is dispensed with in the embodiment of FIG. 6, liquid-tight closing of the inner space is nevertheless advantageous since penetration of water and the resultant corrosion are avoided.

Although the present invention has been described in connection with a plurality of preferred embodiments thereof, many other variations and modifications will now become aparent to those skilled in the art. It is preferred, therefore, that the present invention be limited not by the specific disclosure herein, but only by the appended claims.

What is claimed is:

1. A press roll for forming a press nip with a counter roll, the press roll having lateral ends and comprising;

a main support member, which extends along the press roll between respective opposite lateral ends thereof; means for supporting the support member;

an endless, flexible, liquid-impervious press jacket comprising a fabric-reinforced, relatively hard plastic material, wrapped around the support member, the press jacket having opposite lateral ends; the jacket being rotatable on the support member and past the counter roll; means on the support member for urging the press jacket outwardly toward the counter roll;

a respective press jacket support element at each of the lateral ends of the roll and outside the lateral ends of the support member; each support element having a periphery and also having an outwardly facing outside end; the press jacket support element being rotatable with the press jacket;

at each lateral end thereof, the press jacket having an edge zone which extends past the periphery of the respective support element and then extends radially inwardly past the outside end of the support element, and the jacket there defining an annular end sealing surfae;

clamping means located outward of the outside and of at least one of the jacket support elements for being clamped against the annular end sealing surfce of the press jacket and for clamping that end sealing surface against the outside end of the one support element to form a liquid-tight seal; and at least one longitudinal end thereof, the jacket edge zone being urged radially inwardly toward the axis of the press roll for forming the end sealing surface of the edge zone.

2. The press roll of claim 1, wherein the support member is supported stationary, and the press jacket is rotated over the support member in its contact with the counter roll.

3. The press roll of claim 1, wherein the support member is supported to rotate together with the press jacket.

4. The press roll of claim 3, wherein the press jacket itself serves as a covering of the rotatable support member.

5. The press roll of claim 1, wherein a press nip is defined at the support member where it is opposite the counter roll; the outside ends of the jacket support elements being laterally beyond the press nip.

6. The press roll of claim 1, further comprising a plurality of biasing means distributed around the roll for urging the edge zone of the press jacket radially inwardly at the one jacket support element.

7. The press roll of claim 6, wherein the biasing means comprise tensioning elements.

8. The press roll of claim 7, wherein there are at least 30 tensioning elements distributed around the roll.

9. The press roll of claim 7, wherein the edge zone of the jacket is formed into a plurality of tongues extending longitudinally outwardly of the jacket and a respective cutout being defined between each two neighboring tongues around the lateral edge of the press jacket;

a respective one of the tensioning elements being applied to each of the plurality of tongues for urging the tongues radially inwardly.

10. The press roll of claim 9, wherein the clamping means at the outside end of the one jacket support element comprises a clamping flange; the clamping flange being annular and having a radially inner circumference;

the tongues being long enough to the ends of the tongues that the radial distance from the axis of the roll to radially inner circumference of the clamping flange is greater than the radial distance from the axis of the roll to the ends of the tongues.

11. The press roll of claim 10, wherein the clamping flange is divided into a series of segments of an annulus.

12. The press roll of claim 9, wherein the outside end of the one jacket support element has a plurality of outward projections defined on it, and each being placed for being received in a respective one of the cutouts of the press jacket; the cutouts each having a base, and the projections being so placed that the cutouts bases rest against the respective projections for centering the jacekt on the support member and the jacket support element.

13. The press roll of claim 12, wherein the clamping means at the outside end of the one jacket support element comprises a clamping flange; a plurality of clamping screws distributed over the clamping flange for fastening the clamping flange to the outside end of the support element for clamping the edge zone; the screws being disposed between tongues around the clamping flange;

a first plurality of the projections being comprised by the screws; the screws alternating around the circumference with a second plurality of the projections.

14. The press roll of claim 13, wherein all cutouts in the jacket are of the same shape; the screws and the projections of the second plurality having the same respective cross sections.

15. The press roll of claim 14, wherein all of the cutouts are of the same depth, and all of the screws and the projections are at the same radial distance from the axis of the roll.

16. The press roll of claim 12, wherein all of the cutouts are of the same depth, and all of the projections are at the same radial distance from the axis of the roll.

17. The press roll of claim 9, wherein the clamping means at the outside end of the support element comprises a clamping flange; a plurality of clamping screws being distributed over the clamping flange for fastening the clamping flange to the outside end of the support element for clamping the edge zone; and the screws being disposed between the tongues around the clamping flange.

18. The press roll of claim 9, wherein the clamping flange has a plurality of projections on it and extending to the one jacket support element, and the one jacket support element having a recess therein for receiving the clamping flange projections for centering the clamping flange on the one jacket support element; the clamping flange projections projecting through the cutouts between the tongues.

19. The press roll of claim 6, further comprising an annular centering surface defined on and projecting from the outside of the jacket support element, and the lateral end edge of the edge zone of the press jacket being radially inwardly biased against the annular centering surface for centering the jacket on the support member and on the jacket support element.

20. The press roll of claim 6, wherein the clamping means at the outside end of the support element comprises a clamping flange; a plurality of clamping screws distributed over the clamping flange for fastening the clamping flange to the outside end of the support element for clamping the edge zone; the biasing means being disposed between the screws around the clamping flange.

21. The press roll of claim 1, further comprising, at at least one of the lateral ends, a plurality of tongues being formed on the edge zone of the jacket;

the clamping means at the outside end of the support element comprising a clamping flange; the tongues being inserted between the clamping flange and the outside end of the support element, and the jacket having a rounded transition to enable the insertion of the tongues; the rounded transition also being urged into the space between the clamping flange and the outside and before the clamping flange clamps.

22. The press roll of claim 21, wherein the clamping flange has a plurality of projections on it and extending to the one jacket support element, and the one jacket support element having a recess therein for receiving the clamping flange projections for centering the clamping flange on the one jacket support element; the clamping flange projections projecting through the cutouts between the tongues.

23. The press roll of claim 22, wherein the clamping flange is divided into a series of segments of an annulus.

24. The press roll of claim 1, wherein the clamping flange is divided into a series of segments of an annulus.

25. The press roll of claim 1, wherein the press jacket is comprised of a hard reinforced polyurethane plastic material.

*26. A press jacket for forming the exterior of a press roll which forms a press nip with a counter roll, the press jacket comprising:*

*an endless, flexible, liquid-impervious press jacket for being wrapped around and being rotatable on a press roll support member that has a respective rotatable press jacket support element with a periphery at each press roll end;*

*the endless press jacket having opposite lateral ends; at at least one of the lateral ends, the press jacket having an edge zone for extending past the periphery of the respective support element and for then extending radially inward, thereby to define an annular end sealing surface at the respective end zone of the press jacket;*

*at least one edge zone of the press jacket being formed into a plurality of tongues which are adapted for extending laterally outward of the jacket and which then are adapted for extending radially inward past the outside of the support element, with a respective cutout being defined between each two neighboring tongues around the lateral edge zone of the press jacket.*

*27. The press jacket of claim 26, wherein the press jacket is comprised of fabric reinforced, relatively hard, plastic material.*

*28. The press jacket of claim 27, wherein the plastic material press jacket is comprised of polyurethane.*

*29. The press jacket of claim 26, and further comprising a respective tensioning element applied to each of the tongues of the plurality thereof for urging the tongues radially inwardly.*

*30. The press jacket of claim 26, wherein there is an edge zone at each lateral end of the press jacket and there is a respective plurality of the tongues at each lateral edge zone of the press jacket.*

* * * * *